(12) United States Patent
Vetelino et al.

(10) Patent No.: US 7,788,979 B2
(45) Date of Patent: Sep. 7, 2010

(54) MONOLITHIC ANTENNA EXCITED ACOUSTIC TRANSDUCTION DEVICE

(75) Inventors: John F. Vetelino, Veazie, ME (US); Donald F. McCann, Holden, ME (US)

(73) Assignee: University of Maine System Board of Trustees, Bangor, ME (US)

(*) Notice: Subject to any disclaimer, the term of this patent is extended or adjusted under 35 U.S.C. 154(b) by 561 days.

(21) Appl. No.: 11/823,135

(22) Filed: Jun. 27, 2007

(65) Prior Publication Data
US 2008/0156098 A1 Jul. 3, 2008

Related U.S. Application Data

(60) Provisional application No. 60/817,803, filed on Jun. 30, 2006.

(51) Int. Cl.
*G01N 29/036* (2006.01)
*G01N 29/02* (2006.01)

(52) U.S. Cl. .................. 73/579; 73/19.03; 73/24.06; 73/32 A; 73/54.26; 73/54.41; 73/61.79; 73/64.53

(58) Field of Classification Search ............... 73/19.03, 73/24.01, 24.06, 31.06, 32 A, 54.23, 54.24, 73/54.25, 54.26, 54.41, 61.49, 61.75, 61.79, 73/64.52, 64.53, 579
See application file for complete search history.

(56) References Cited

U.S. PATENT DOCUMENTS

| | | | | |
|---|---|---|---|---|
| 3,609,416 A | * | 9/1971 | Epstein | ............ 310/313 B |
| 4,789,804 A | * | 12/1988 | Karube et al. | ............... 310/311 |
| 5,416,448 A | | 5/1995 | Wessendorf | |
| 5,455,475 A | | 10/1995 | Josse et al. | |
| 5,744,902 A | | 4/1998 | Vig | |
| 5,852,229 A | | 12/1998 | Josse et al. | |
| 5,869,748 A | * | 2/1999 | Stevenson et al. | ........ 73/53.01 |
| 5,869,763 A | | 2/1999 | Vig et al. | |
| 6,247,354 B1 | | 6/2001 | Vig et al. | |
| 6,260,408 B1 | | 7/2001 | Vig et al. | |
| 6,293,136 B1 | | 9/2001 | Kim | |
| 6,755,073 B2 | | 6/2004 | Jakoby et al. | |
| 6,903,626 B2 | | 6/2005 | Tsutsumi et al. | |
| 2003/0076743 A1 | | 4/2003 | Thompson et al. | |
| 2005/0003560 A1 | | 1/2005 | Zeng et al. | |
| 2005/0039532 A1 | | 2/2005 | Ohsugi et al. | |
| 2005/0103096 A1 | | 5/2005 | Jakoby et al. | |

FOREIGN PATENT DOCUMENTS

| | | |
|---|---|---|
| EP | 0 521 380 | 1/1993 |
| EP | 0 841 708 | 5/1998 |

(Continued)

OTHER PUBLICATIONS

Yihe Hu et al., A Lateral Field Excited Liquid Acoustic Wave Sensor, paper presented at the 2003 IEEE International Ultrasonics Symposium, Oct. 5-8, 2003, Honolulu, Hawaii.

*Primary Examiner*—Hezron Williams
*Assistant Examiner*—Rose M Miller
(74) *Attorney, Agent, or Firm*—MacMillan, Sobanski & Todd, LLC

(57) ABSTRACT

A Monolithic Antenna Excited Acoustic Transduction (MAEAT) device is fabricated by photolithographically depositing a metallic antenna on one side of a piezoelectric crystal substrate.

25 Claims, 11 Drawing Sheets

FOREIGN PATENT DOCUMENTS

| | | |
|---|---|---|
| JP | 2004129185 | 4/2004 |
| JP | 2005092490 | 4/2005 |
| WO | WO 84/01830 | 5/1984 |
| WO | WO 97/45723 | 12/1997 |
| WO | WO 03019981 A2 * | 3/2003 |
| WO | WO 2004109272 A1 * | 12/2004 |
| WO | WO 2006064211 A1 * | 6/2006 |

* cited by examiner

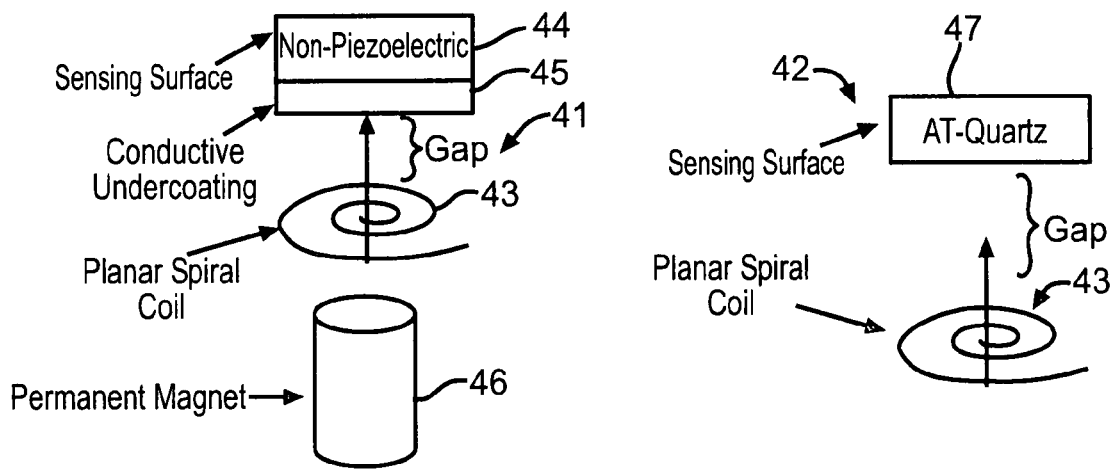
FIG. 6
(PRIOR ART)
FIG. 7
(PRIOR ART)
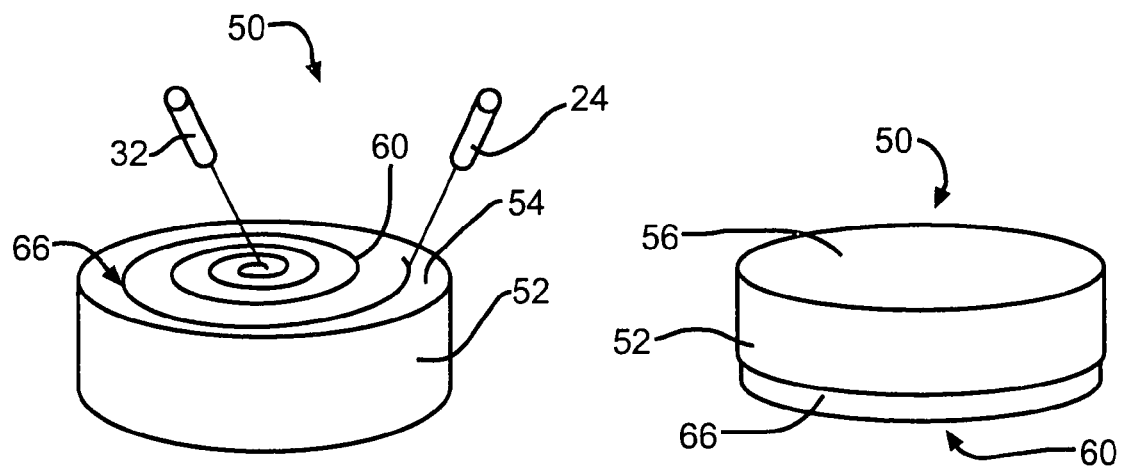
FIG. 8
FIG. 9

MONOLITHIC ANTENNA EXCITED ACOUSTIC TRANSDUCTION DEVICE

CROSS-REFERENCE TO RELATED APPLICATIONS

This application claims the benefit of U.S. Provisional Application No. 60/817,803, filed Jun. 30, 2006, the disclosure of which is incorporated herein by reference.

BACKGROUND OF THE INVENTION

This invention relates in general to acoustic devices and in particular to an acoustic wave device having a piezoelectric substrate that utilizes a monolithic antenna to excite acoustic waves in the substrate.

Piezoelectric materials, such as crystalline quartz, generate an electric field or voltage when subjected to mechanical stress, and conversely, generate mechanical stress when subjected to an electric field or voltage. Accordingly, piezoelectric materials have proven useful in many diverse technologies. Typically, electrodes are deposited upon the surface of the crystal and an AC voltage is applied to the electrodes to generate an electric field in the crystal. The electric field, in turn, generates mechanical stresses in the crystal. If the applied AC voltage is at or near the resonant frequency of the crystal, or overtone harmonics of the resonant frequency, resonant acoustic waves are excited within the crystal. The resonant frequencies are determined by the cut angle, thickness, length, width, and mass of the crystal, and the resonant acoustic waves propagate and resonate within the crystal with very little loss.

A measure of how narrow a band of frequencies can be passed through a particular piezoelectric crystal with minimum attenuation relative to the resonant frequency of the crystal is referred to as the Q of the crystal. The Q of the crystal, which is a function of the crystallographic orientation of the crystal, determines the specific application for the crystal. For example, very low Q crystals are capable of converting wide frequency bands of mechanical energy to electrical energy; and, conversely, wide frequency bands of electrical energy to mechanical energy. Thus, low Q materials are often used as sonic transducers in microphones or speakers because the low Q allows many tones to be produced. With a very high Q material, only a very narrow band of frequencies may be passed through the crystal. Thus, high Q material is typically used in devices that require highly accurate frequency control, such as oscillators.

High Q piezoelectric materials also are used in sensors. With modern manufacturing methods, precision crystals of quartz or other similar very high Q material may be made to oscillate at a frequency that is accurate to within a few parts per million or less. During production of such quartz resonators, layers of conductive electrode material may be deposited with a precision of a few atomic layers. The resonant frequency of the resulting resonators will be sensitive to extremely small changes in the mass of the electrodes. This characteristic sensitivity of high Q piezoelectric materials to changes in mass has led to a number of diverse sensor applications. For example, a quartz resonator may be coated with a sorbent that is selective to a particular compound. The amount, or concentration, of the compound can then be determined by monitoring the change in the resonant frequency of the quartz crystal as the compound is absorbed by the sorbent since, as the compound is absorbed, the mass of the sorbent and, hence, the total mass of the vibrating structure increases. Because the addition or subtraction of mass to the piezoelectric material results in a change of the resonant frequency of the crystal, such devices are commonly referred to as a Quartz Crystal Microbalances (QCM's) and are widely used in applications where a change in mass, density or viscosity is monitored, such as in sensing applications.

Referring now to the drawings, a typical known QCM sensor is illustrated generally at 10 in FIGS. 1 and 2. The sensor 10 includes a disc shaped substrate 12 of quartz having a diameter of approximately 25 mm. The standard crystallographic orientation used is an AT-cut since it is a temperature stable orientation in which only a Transverse Shear Mode (TSM) acoustic wave can be excited. Other orientations in quartz in which only a TSM acoustic wave can be excited also may be utilized. FIG. 1 shows the reference surface 14 of the substrate while FIG. 2 shows the sensing surface 16 of the substrate 12 that is opposite from the reference surface 14. A disc shaped reference electrode 18 formed from an electrically conducting material and having a diameter of approximately 6 mm is deposited upon the center of the reference surface 14. The electrode 18 is formed from an electrically conductive metal. The reference electrode 18 is connected by a first strip 20 of conductive material to an arcuate reference electrode tap 22. The reference electrode tap 22 allows electrical connection to an external sensing circuitry (not shown). The electrical connection is illustrated by a wire lead 24; however, the lead 24 is intended to be exemplary and other types of conventional electrical connections may be utilized.

As shown in FIG. 2, a disc shaped sensing electrode 26 formed from an electrically conductive metal and having a diameter of approximately 13 mm is deposited upon the center of the sensing surface 16. A second strip of conductive material 28 extends from the sensing electrode 26 to the edge of the sensing surface 16, transversely across the side of the substrate 12 and onto the reference surface 14, as shown in FIG. 1, where it ends in an arcuate sensing electrode tap 30. Similar to the reference electrode tap 22, the sensing electrode tap 30 allows electrical connection to the external sensing circuitry (not shown), as illustrated by a wire lead 32. Additionally, an adhesive layers 33 and 34 are typically deposited between the electrodes, 18 and 26, the corresponding substrate surface, 14 and 16, respectively, to enhance adherence of the electrodes to the substrate surface. Finally, depending upon the application, a sorbent selective film (not shown) may cover the sensing surface 16.

During operation of the sensor 10, a variable frequency oscillator (not shown) is electrically connected to the reference and sensing electrode taps, 22 and 30, and the sensing surface 16 is inserted into an environment, which may be either a gas or a liquid, while the reference surface 14 remains exposed to air. The environment contains a measurand, which is a specific property of the environment that is being sensed by the sensor, such as, for example the concentration of a certain substance within a gas or liquid. Thus, when the sensing surface 16 is inserted into an environment, the sensing surface is exposed to a specific measurand contained within the environment. Should the sensing surface be covered by a sorbent film, the sorbent film also is immersed in the environment. The oscillator applies a varying voltage to the electrodes, 18 and 26, which then generate acoustic waves within the substrate 12. Such a mode of operation is referred to as Thickness Field Excitation (TFE). Before exposing the sensing surface 16 to the measurand the sensor 10 is calibrated by varying the oscillator frequency to resonate the sensor 10. The resonance frequency is detected and stored in a conventional device or circuit (not shown). After calibration, the sensing surface is inserted into the environment being monitored. The effect of mechanical loading properties of the measurand, such as mass, density and viscoelasticity, upon the sensing surface 16 causes the resonant frequency of the sensor to shift. The shift in resonant frequency can be calibrated to be indicative of the magnitude of a specific mechanical loading property of the measurand.

Alternate embodiments of the QCM sensor 10 having different sensing electrodes are illustrated in FIGS. 3 through 5. FIG. 3 illustrates small electrode geometry with a very small circular sensing electrode 35. A typical diameter for the sensing electrode 35 would be about 0.8 mm. In FIG. 4, a closed ring geometry sensing electrode 36 that has an aperture formed through the center of the electrode disc is shown, while FIG. 5 illustrates an open ring sensing electrode 38. The open ring electrode 38 is very similar to the closed ring electrode 36, except that the open ring electrode 38 has a slot 40 extending through the ring that corresponds to the tap region of the reference electrode. Both the closed and open ring electrodes 36 and 38 have an outside diameter of approximately 13 mm and an inside diameter of approximately 11 mm. All of the sensors shown in FIGS. 4 through 5 have a reference surface configuration that is similar to the sensor 10 shown in FIG. 1.

The use of conventional QCM sensors, such as the one shown in FIGS. 1 and 2, is limited to applications only the mechanical properties listed above are measured. In addition, the resonant frequency of the device is limited to the fundamental frequency of the device, which limits the sensitivity of the device. In many applications, the measurement of changes in the electrical properties is critical. However, with conventional QCM sensors, such as the one shown in FIGS. 1 and 2, the sensing electrode 26 that contacts the measurand is the same size or larger than the reference electrode 18 that contacts air. Because of its size, the sensing electrode 26 shields most of the TSM electric field, preventing the penetration of the field into the measurand. Thus, a conventional QCM sensor has minimal sensitivity to changes in electrical properties of the measurand. The modified sensing electrode geometries shown in FIGS. 3 through 5 reduce the size of the sensing electrode. As a result, a small shift of the resonant frequency of the modified QCM sensors may be detected as the electrical properties of the measurand changes.

In order to allow Transverse Shear Mode (TSM) electrical fields to penetrate, a sensing surface of a AT-cut quartz substrate that is exposed to liquid or gas should be bare. Such a bare sensing surface can be achieved by placing both electrodes upon a reference surface, that is opposite from the sensing surface, to provide a Lateral Field Excited (LFE) sensor. The details regarding such a LFE sensor and application of this sensor to detect phosmet and *E. coli* are described in U.S. Pat. No. 7,075,216, which is incorporated herein by reference.

In contrast to QCM and LFE sensors, it is also known to utilize a spiral coil as the excitation source to form two other acoustic wave sensors, namely a Magnetic Acoustic Resonant Sensor (MARS) 41, as shown in FIG. 6, and an Electromagnetic Piezoelectric Acoustic Transduction Sensor (EMPAS) 42, as shown in FIG. 7.

The MARS 41 utilizes the same basic configuration and operating principles as an Electromagnetic Acoustic Transducers (EMAT), a technology that has been used for more than 50 years on the macro scale to test the structural integrity of metallic objects such as sheet metal and materials characterization, but applies it on the micro scale to excite an acoustic wave. In the configuration of the MARS 41 shown in FIG. 6, an electrically excited hand wound spiral coil 43 is placed near, but spatially separated from, a non-piezoelectric substrate 44 that carries a metalized conductive coating, or metal layer, 45 disposed upon the surface of the substrate 44 that is adjacent to the coil 43. Thus, an air gap separates the coil 43 from the surface of the metal layer 45. The substrate 44 is exposed to a permanent magnetic field generated by an adjacent permanent magnet 46. The wound spiral coil 43 produces electromagnetic fields that induce eddy currents on the thin metal layer 45 that is attached to the substrate 44. The permanent magnet 46 produces static magnetic fields that couple with the time-varying eddy currents to produce time varying Lorentz forces within the metal layer 45. These time varying Lorenz forces produce time-time varying stresses and hence acoustic waves within the substrate 44. As with other acoustic wave sensors the resonant frequency of the MARS 41 shifts with changes on its sensing surface. Unlike other acoustic wave sensors however, the MARS configuration has the advantage of utilizing non-piezoelectric substrates such as aluminum, silica glass, sapphire and high-Q silicon membranes.

The EMPAS 42 shown in FIG. 7 utilizes a piezoelectric crystal as a substrate 47 and a hand wound spiral coil 43 that is separated by a small air gap of approximately 30 mm from the substrate. A thin plastic o-ring (not shown) is placed between the coil 43 and the substrate 47, resulting in the small air gap between the coil and crystal. The spiral coil 43 produces electric fields that penetrate the piezoelectric material to excite acoustic waves within the substrate 47. The EMPAS 42 has been shown to operate at frequencies up to 700 MHz.

In both the MARS 41 and EMPAS 42, the sensor configurations are not monolithic and contain several components that may result in poor reproducibility of sensor properties from sensor to sensor. Furthermore, in both the MARS and EMPAS sensors, the spiral coils are hand wound and are separated from the substrate by an insulating layer of air. Although these sensors have been shown to operate at frequencies of approximately 700 MHz, reproducibility of sensor properties from device to device is problematic. Because increased accuracy of sensors is desirable, it would be desirable to devise a device having an improved geometry.

BRIEF SUMMARY OF THE INVENTION

This invention relates to a Monolithic Antenna Excited Acoustic Transduction (MAEAT) device.

The present invention contemplates a monolithic spiral coil acoustic transduction (MSCAT) sensor that is an example of a MAEAT device and that combines and improves upon the positive features of bulk acoustic wave (BAW) sensors such as the Quartz Crystal Microbalance (QCM) and other acoustic sensors. The MSCAT sensor includes a substrate formed from a piezoelectric material and an exciting antenna formed upon a surface of said substrate. The MSCAT device has many advantages as a sensor. The MSCAT sensor's exciting electrode configuration is not exposed to the sensing film or environment as in the case of most acoustic wave sensors.

The present invention also contemplates a method for forming a MSCAT sensor that includes the step of providing a piezoelectric crystal and then cutting the crystal to form a substrate having parallel reference and sensing surfaces. An antenna is then deposited upon the reference surface of the substrate.

The present invention further contemplates a test apparatus that includes an acoustic wave device having an exciting antenna formed upon a surface of a substrate formed from a piezoelectric material with the antenna connected to a variable frequency oscillator connected to the exciting antenna. The apparatus also includes a sensing circuit connected to the oscillator and a controller connected to the oscillator and the sensing circuit. The controller is operative to sweep the oscillator through a range of frequencies that include a characteristic frequency of the acoustic device while monitoring a parameter of the acoustic device.

Various objects and advantages of this invention will become apparent to those skilled in the art from the following detailed description of the preferred embodiment, when read in light of the accompanying drawings.

BRIEF DESCRIPTION OF THE DRAWINGS

FIG. 6 illustrates a known Magnetic Acoustic Resonance Sensor (MARS).

FIG. 7 illustrates a known Electromagnetic Piezoelectric Acoustic Sensor (EMPAS).

FIG. 8 is a perspective view of the reference surface of a Monolithic Spiral Coil Acoustic Transduction (MSCAT) sensor that is in accordance with the invention.

FIG. 9 is a perspective view of the sensing surface of the MSCAT sensor shown in FIG. 8.

DETAILED DESCRIPTION OF THE PREFERRED EMBODIMENT

Figure 1:
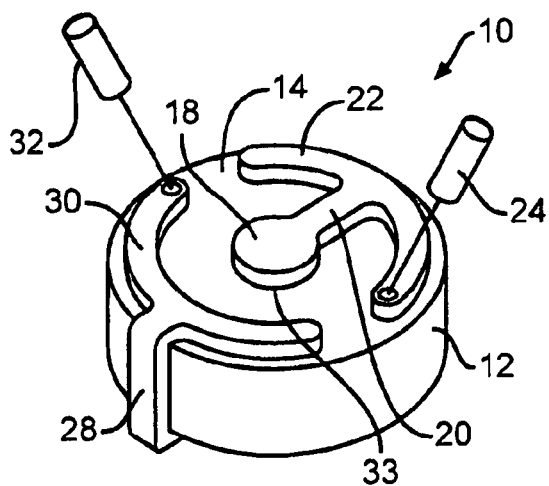
FIG. 1 is a perspective view of the reference surface of a known Quartz Crystal Microbalance (QCM) sensor.
Figure 2:
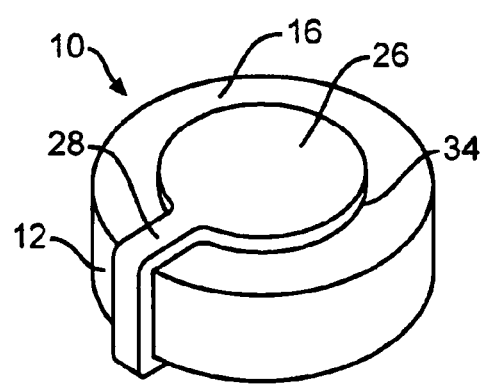
FIG. 2 is a perspective view of the sensing surface of the known QCM sensor shown in FIG. 1.
Figure 3:
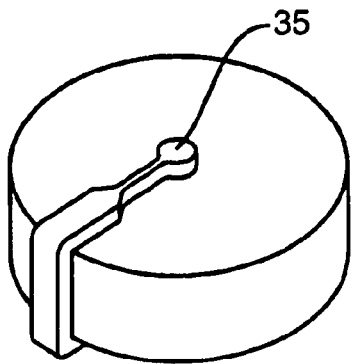
FIG. 3 is a perspective view of an alternate embodiment of the sensing surface of the known QCM sensor shown in FIG. 2.
Figure 4:
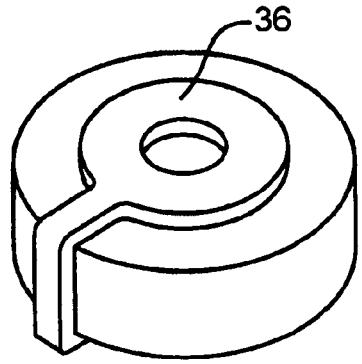
FIG. 4 is a perspective view of another alternate embodiment of the sensing surface of the known QCM sensor shown in FIG. 1.
Figure 5:
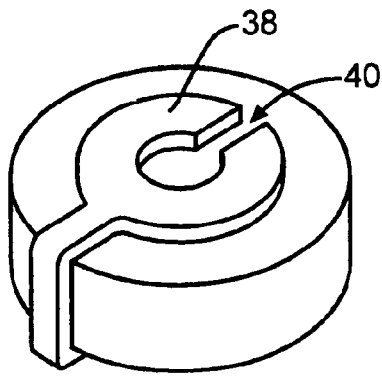
FIG. 5 is a perspective view of another alternate embodiment of the sensing surface of the known QCM sensor shown in FIG. 1.

The present invention concerns a Monolithic Spiral Coil Acoustic Transduction (MSCAT) sensor which is a type of a Monolithic Antenna Excited Acoustic Transduction (MAEAT) device that combines and improves upon the positive features of other acoustic wave sensors that have been developed. Referring again to the drawings, there is illustrated in FIGS. 8 and 9 a MSCAT sensor 50 that is in accordance with the invention. The sensor 50 includes a disc shaped wafer or substrate 52. In the preferred embodiment, AT-cut quartz crystal is used for the substrate 52. Although the particular piezoelectric crystal described in the preferred embodiment is AT-quartz, other crystallographic orientations of quartz, such as, for example, BT, SC, CT, and DT, or orientations in other piezoelectric crystals may be used depending upon the specific application. Examples of other piezoelectric crystals include lithium tantalate, lithium niobate, potassium niobate, gallium phosphate and members of the langasite family of crystals and associated orientations. Also as shown in FIG. 8, the substrate 52 is approximately 0.5 mm thick and 25 mm in diameter; however, the invention may be practiced with substrates having different thickness and/or diameters. For example, the invention contemplates that the substrate thickness would be within a range of approximately 0.3 mm to 1.0 mm. Additionally, the substrate 52 may have a different shape than that which is shown in FIGS. 8 and 9, such as, for example, square, rectangular, polygonal, or elliptical, as show by the dashed lines in FIG. 9A. One circular surface of the substrate 52 is the reference surface 54 of the sensor 50, while the opposite circular surface is the sensing surface 56. The reference and sensing surfaces 54 and 56 are flat and parallel. The inventor has found that the invention performs better when the surfaces are polished and parallel to within a tolerance of four light bands.

Figure 9A:
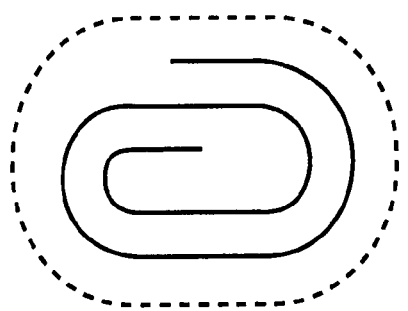
FIGS. 9A through 9E illustrate other embodiments of the sensor shown in FIGS. 8 and 9.
Figure 9B:
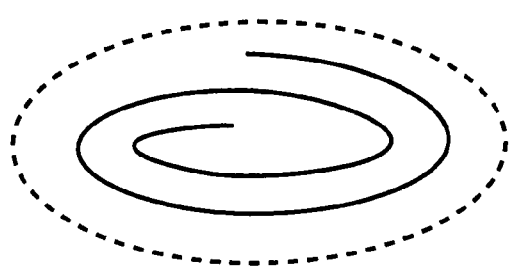
Figure 9C:
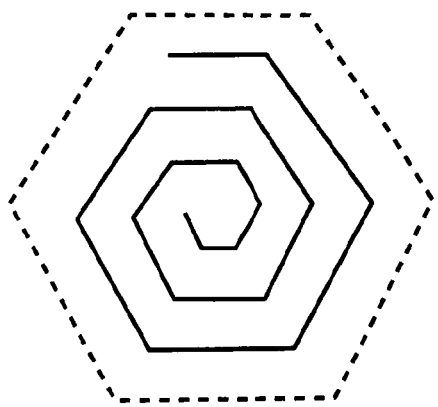
Figure 9D:
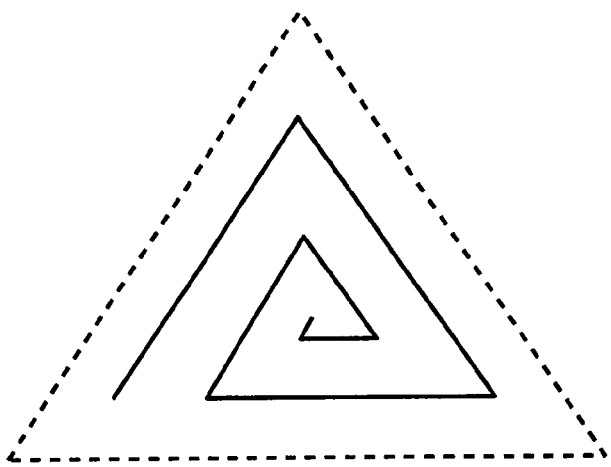
Figure 9E:
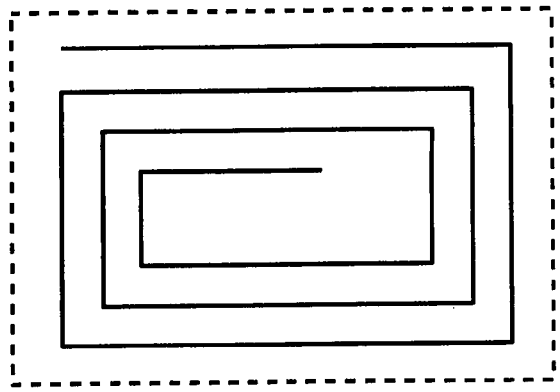

An antenna 60 is deposited upon the reference surface 54 of the substrate 52 by a conventional photolithography process. The antenna 60 is formed from an electrically conductive material, such as a metal. The inventor used a noble metal, such as gold, palladium or platinum, for the antenna 60, because noble metals do not oxidize, thus maintaining their conductivity. However, other metals, such as platinum, silver, copper, zirconium, aluminum, zinc, lead, palladium, chromium, etc. also could be used to form the antenna 60. The specific types of metal used would be dependant on the application. Additionally, the specific geometry of the coil may vary in dimensions and structure. In particular the coil may have a variable number of turns and be of different thicknesses and widths. Also since the coil acts as an antenna to excite acoustic waves in the piezoelectric crystal, configurations other than a spiral coil may be used. As illustrated in FIG. 8, the antenna 60 is shaped as a circular spiral coil; however the antenna may have a non-circular spiral shape, such as for example, an oval shaped spiral as shown in FIG. 9A, an elliptically shaped spiral as shown in FIG. 9B, a polygonal as shown in FIG. 9C, a triangular shaped spiral as shown in FIG. 9D, or a quadrilateral shaped spiral as shown in FIG. 9E. As described above, the substrate for each of the above non-circular antennas may be formed with the same general shape, as illustrated by the dashed lines in FIGS. 9A through 9E. Alternately, the substrate shape may not have the same general shape (not shown), i.e., an antenna having an oval shaped spiral may be deposited upon a circular shaped substrate (not shown). While the antenna thickness for the sensor shown in FIG. 6 is usually between 1,500 and 2,500 Å thick; however, the antenna thickness also may be less than 1,500 Å or more than 2,500 Å.

An adhesive layer 66 is disposed between the antenna 60 and the substrate reference surface 54. The adhesive layer 66, which in the preferred embodiment is a layer of chromium that is about 100 Å thick, enhances the adherence of the antenna 60 to the surface of the substrate 52. Alternately, other materials, such as, for example zirconium or titanium, or alloys of aluminum, zirconium or titanium, also may be utilized to form the adhesive layer 66 as determined by the antenna material and sensor application. The adhesive layer 66 is applied to the substrate 52 by a conventional method before the antenna 60 is deposited thereupon. While the adhesive layer 66 shown in FIG. 6 has a thickness of approximately 100 Å, the invention also may be practiced with an adhesive layer thickness that is within the range of 50 to 150 Å.

A pair of electrically conducting wires 24 and 32 is shown in FIG. 8 electrically connected to the ends of the antenna 60. While the electrical connection is illustrated by a pair of wires 24 and 32, the electrical connections are intended to be exemplary and other types of conventional electrical connections may be utilized, such as, for example, wire bonds. The wires 24 and 32 represent electrical connections to external sensing circuitry, as will be explained below.

The operation of the sensor 50 will now be explained. As shown in FIG. 7, there are no electrodes deposited upon the sensing surface 56. When the spiral coil 60 is energized by an oscillator, the spiral coil 60 acts as an antenna that radiates a time varying electric field that penetrates into the AT-cut quartz wafer/substrate 52. As a result of the piezoelectric effect, the time varying electric field sets up a time varying stress in the wafer/substrate 52 that generates a Transverse Shear Mode (TSM) acoustic wave within the substrate 52. The frequency of excitation is selected to excite resonant acoustic waves at the TSM fundamental and higher order harmonic frequencies within the substrate 52. The resonant frequency for the substrate 52 is a function of the thickness of the wafer and the velocity of acoustic waves in the particular substrate. The acoustic wave includes both mechanical displacements and electric fields that appear upon the substrate sensing surface 56. The absence of electrodes upon the sensing surface 56 allows the mechanical and electric fields generated by the TSM acoustic wave to penetrate into an environment containing a measurand of interest that is adjacent to the sensing surface 56. The penetration of the mechanical and electric fields into the environment results in an increased sensitivity to both mechanical and electrical property changes.

The MSCAT sensor 50 can operate at high frequencies by efficiently exciting high harmonics with the application of a high frequency Radio Frequency (RF) signal to the spiral coil 60. The MSCAT sensor also potentially may operate at very high frequencies (over 1 GHz) by efficiently exciting high harmonics with the application of a high frequency RF signal to the spiral coil. The inventor has found that resonant acoustic waves up to the $63^{rd}$ order harmonic can be efficiently excited. As described below, the MSCAT sensor 50 was used to measure the viscosity of a solution of corn syrup in deionized water. When compared to the performance of a standard prior art Quartz Crystal Monitor (QCM), the MSCAT sensor 50 was found to be over three times more sensitive to viscosity changes and five times more sensitive in the detection of E. coli. The MSCAT sensor 50 was also shown to be capable of detecting conductivity changes in liquids.

As described above, when the antenna is formed as a circular spiral in functional block 76, a MSCAT sensor results. Generally, any sensor that is excited by an antenna, regardless of the shape of the antenna may be referred to as a Monolithic Antenna Excited Acoustic Transduction (MAEAT) sensor. Thus, the MSCAT sensor described above actually is an example of a MAEAT sensor. While the present invention has been illustrated and described in terms of a MSCAT sensor, it will be appreciated that the invention may also be practiced with MAEAT sensors. In addition to having sensor applications the invention also may be utilized as a MAEAT device that has application as a stand-alone or fundamental component of a high frequency signal processor such as, for example, a filter.

Figure 12:
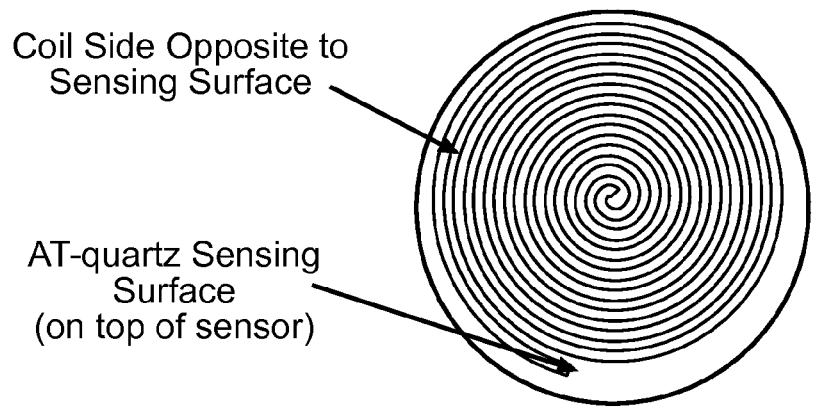
FIG. 12 illustrates the geometry of a Monolithic Spiral Coil Acoustic Transduction (MSCAT) sensor.

The Monolithic Spiral Coil Acoustic Transduction (MSCAT) illustrated in FIGS. 8, 9 and 12, does not have a coil separated from the substrate by an air gap, as described above for prior art MARS and EMPAS sensors. As also described above, the MSCAT sensor utilizes only a photolithographically deposited spiral coil on the reference surface making the entire sensor a single piece or monolithic. The MSCAT sensor is novel because, unlike the exciting multiple electrodes utilized upon QCM sensors. the single coil on the MSCAT sensor is an antenna radiating a time varying electric field that penetrates the AT-quartz wafer.

Figure 13:
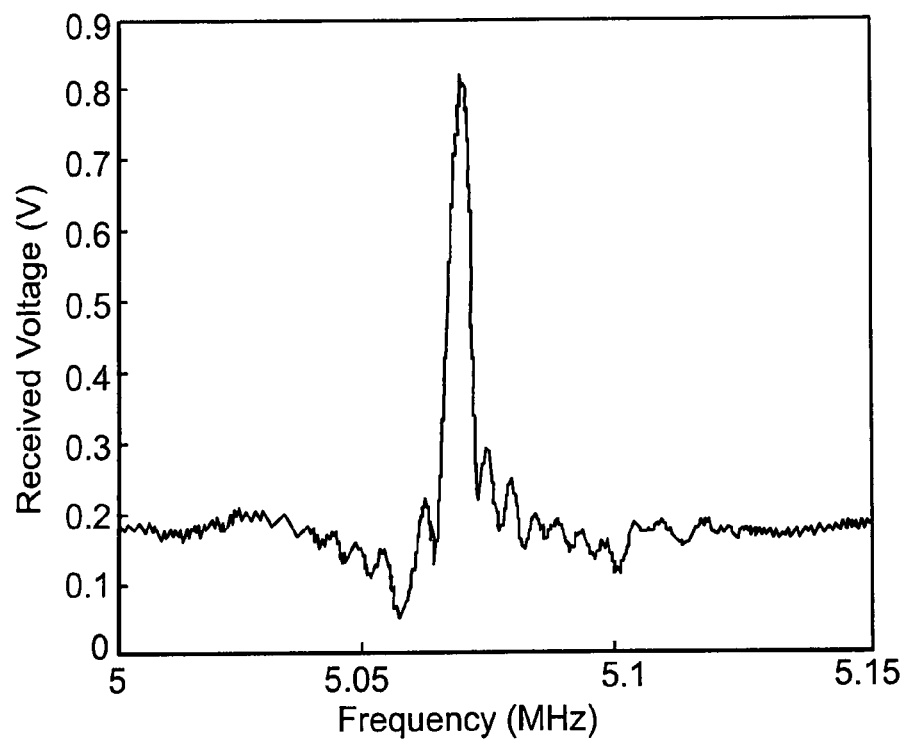
FIG. 13 illustrates the response of a MSCAT sensor at Transverse Shear Mode (TSM) fundamental frequency with deionized water on the surface of the sensor.
Figure 14:
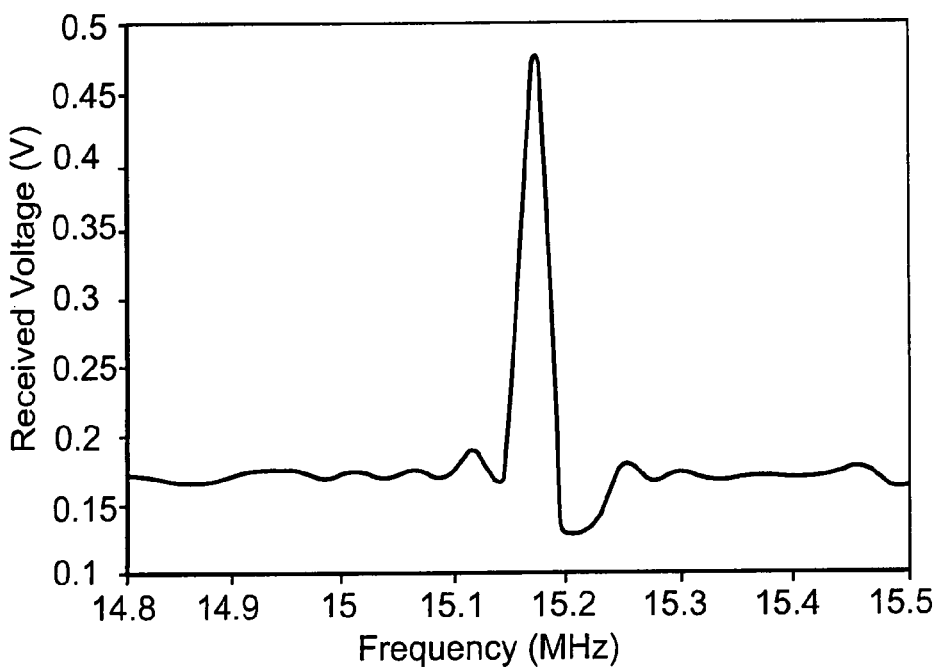
FIG. 14 illustrates the response of a MSCAT sensor at TSM $3^{rd}$ harmonic frequency with deionized water on the surface of the sensor.

Since quartz is a piezoelectric material, the time varying electric field sets up a time varying stress in the wafer. Depending upon the wafer thickness and the frequency of excitation, resonant acoustic waves at the Transverse Shear Mode (TSM) fundamental and higher order frequencies are excited, as illustrated in FIGS. 13 and 14. The frequencies of these resonant modes change when a target analyte is added, or removed from, the sensing surface of the sensor. Hence, a change, or shift, in the resonant frequency of the sensor is a direct measure of the analyte concentration. Since the sensitivity of Bulk Acoustic Wave (BAW) devices increase as the operating frequency increases, the MSCAT sensor, when operated at high order harmonics of the resonant frequency, is significantly more sensitive than standard QCM sensors which can only operate at their fundamental frequency.

Additionally, the MSCAT sensor outperforms the MARS and the EMPAS sensors because:

(1) The MSCAT sensor coil is in direct contact with either the AT quartz substrate or the adhesive layer deposited upon the AT quartz substrate, eliminating any transmission losses due a gap between the coil and sensor substrate;

(2) The MSCAT sensor coil is reproducible due to the photolithographic deposition of the coil;

(3) Photolithographic deposition of the coil eliminates any acoustic wave that occur with the prior art MARS and EMPAS sensors; and (4) The MSCAT sensor is a single component monolithic sensor while the MARS and EMPAS sensors are multi-component sensors that are thereby more prone to damage.

In summary, the MSCAT sensor has the positive features of a photolithographically deposited coil antenna that is isolated from the sensing environment and has the capability of detecting both mechanical and electrical property changes due to a target analyte. This novel device produces a reliable, reproducible sensor in an easy to manufacture package.

The present invention also contemplates a method for fabricating the sensor 50. The method illustrated by the flow chart shown in FIG. 10. In functional block 70 a crystalline piezoelectric material is selected for the substrate. As described above, the material is selected from a piezoelectric crystal such as quartz, lithium tantalite, lithium niobate, potassium niobate, gallium phosphate and members of the langasite family of crystals. In functional block 72, the selected crystal is cut at angles relative to its crystalline axes that correspond to the intended use and resonant frequency. Depending upon the intend use, a cut relative to one crystalline axis, two of the axes, or all three of the axes may be used. The substrate is then shaped to its final size and shape, which also are selected with regard to the desired resonant sensor frequency.

In functional block 74, the crystalline substrate reference surface is optionally polished to assure that the surfaces are sufficiently parallel and smooth and an adhesion layer is deposited by conventional methods upon the reference surface. Then, in functional block 76, the antenna is deposited upon the adhesion layer by conventional photo-lithography techniques. As described above, when the antenna is formed as a circular spiral in functional block 76, a MSCAT sensor results; and. when the antenna is formed with a non-circular shape, a MAEAT sensor results.

Figure 10:
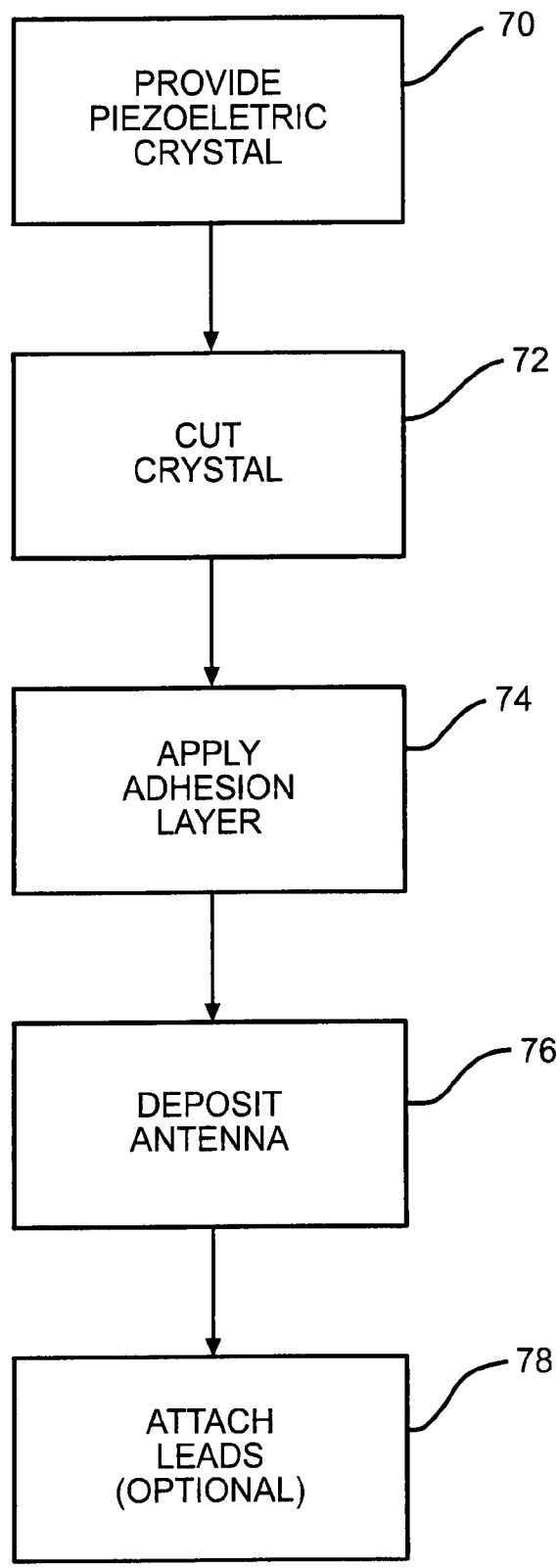
FIG. 10 is a flow chart illustrating a method for fabricating the MSCAT sensor shown in FIGS. 6 and 7.

As shown in FIG. 10, electrical leads are attached to the antenna in functional block 78; however, this step is optional and its inclusion depends upon the method for electrical connecting the sensor to other components. For example, wire bonding may be used, in which case electrical leads would not be needed.

Figure 11:
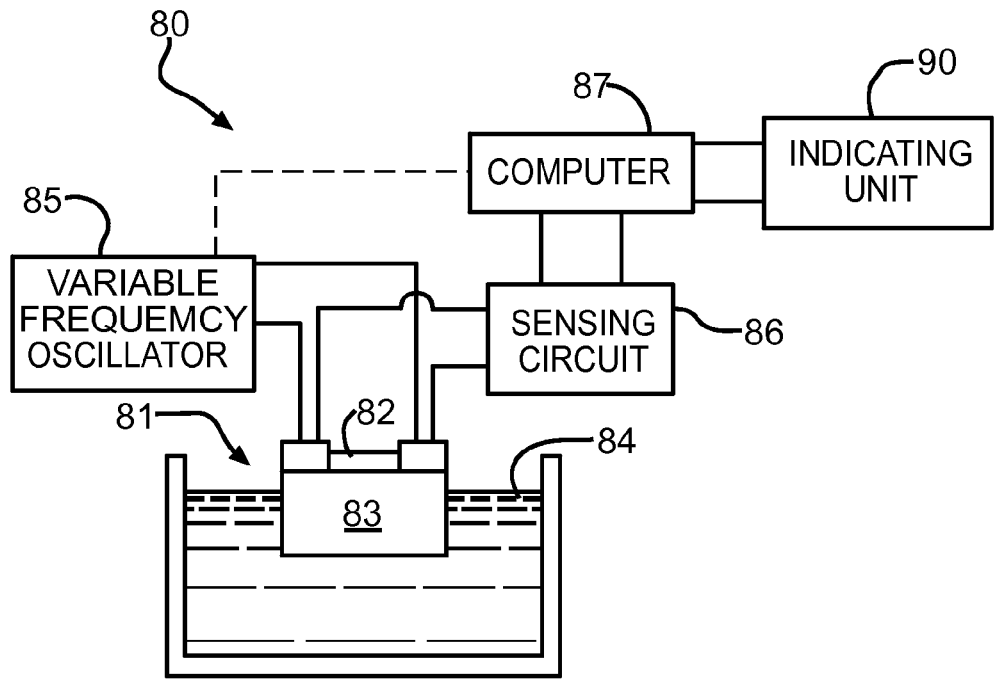
FIG. 11 is a block diagram of a sensing apparatus that includes the MSCAT sensor shown in FIGS. 8 and 9.

The invention also contemplates an apparatus 80 for measuring electrical characteristics of an environment that includes a MAEAT sensor 81 having an antenna 82 disposed upon a substrate 83. A block diagram of the apparatus 80 is shown in FIG. 11 where the sensing surface of the sensor substrate 83 is immersed in an environment 84 that contains a measurand of interest. While the measurand has been described as being contained within the environment, it will be appreciated that the measurand also may be a characteristic of the environment, such as, for example the conductivity of a liquid. While the environment 84 is shown as a liquid in FIG. 11, it will be appreciated that the environment also may be a gas (not shown). The apparatus 80 also includes a commercially available oscillator 85 that drives the MAEAT sensor 81 over a range of frequencies spanning all resonant and anti-resonant frequencies.

A sensing circuit 86 is also connected to the MAEAT sensor 81. The sensing circuit 86 is operative while the oscillator 85 sweeps a narrow band of frequencies near a series resonance frequency, $f_s$ for the MAEAT sensor 81. A variety of known analog or digital circuits, such as, for example, an electrical frequency counter, can be utilized as the sensing circuit 86.

The sensing circuit 86 is connected to a computer 87 that is operative to determine shifts of the resonant frequency, $f_s$, in response to the exposure of the sensor sensing surface to the measurand contained within the environment 84. The computer 87 can be a personal computer, a microprocessor, or an Application Specific Integrated Circuit (ASIC). The computer 87 also may be connected to the oscillator 85 as shown by the dashed line in FIG. 11. When so configured, the computer 87 functions as a controller for the apparatus and provides control signals to initiate the frequency sweeps of the oscillator 85. The computer 87 also compares the sensed critical frequencies with stored reference frequencies to determine changes in the measurand.

The apparatus 80 further includes an indicator unit 90 connected to the computer 87. The indicator unit 80 displays test results generated by the computer 87. In will be appreciated that the apparatus 80 shown in FIG. 11 is intended to be exemplary and other apparatuses may be used.

The operation of the apparatus 80 will now be described with the MAEAT sensor 81 configured as a MSCAT. As described above, the oscillator 85 sweeps a narrow band of frequencies containing the sensor resonant frequency $f_s$, or the harmonic of the sensor resonant frequency that is of interest. For example, the frequencies swept can be between 4.95 MHz and 5.05 MHz for a MSCAT sensor having a series resonant fundamental frequency $f_s$ of about 5.00 MHz, as for the sensor 50 described above. As the oscillator 85 sweeps the frequency band, the sensing circuit 86 monitors, or measures, values of the resonant frequencies and magnitudes and/or phases the sensor impedance over the frequency range. The sensing circuit 86 also may, depending upon the specific circuit, sensor, or measure, magnitudes and/or phases of the sensor admittance over the frequency range to determine anti-resonant frequencies associates with the admittance. The computer 87 correlates shifts in the resonant frequency with stored data. Additionally, the computer may use the sensed impedance magnitude and/or phase to refine the correlation. The differences or similarities of the sensed data with the stored data are indicative of electrical properties of the measurand. The results of the correlation are then displayed upon the indicator unit 90.

Figure 20:
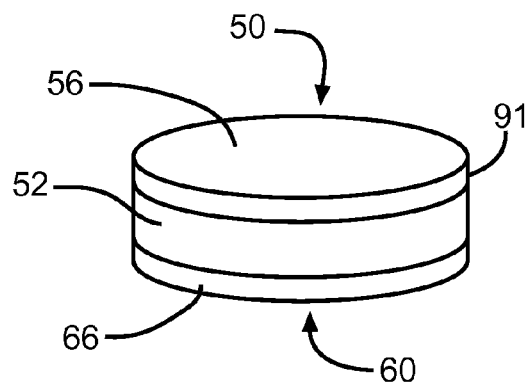
FIG. 20 illustrates a metallic layer deposited upon the sensing surface of the sensor shown in FIG. 9.
Figure 21:
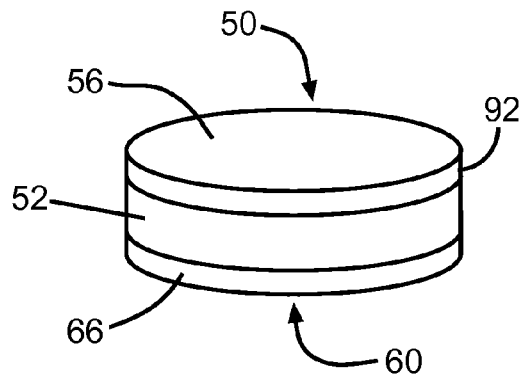
FIG. 21 illustrates a sorbent material deposited upon the sensing surface of the sensor shown in FIG. 9.
Figure 22:
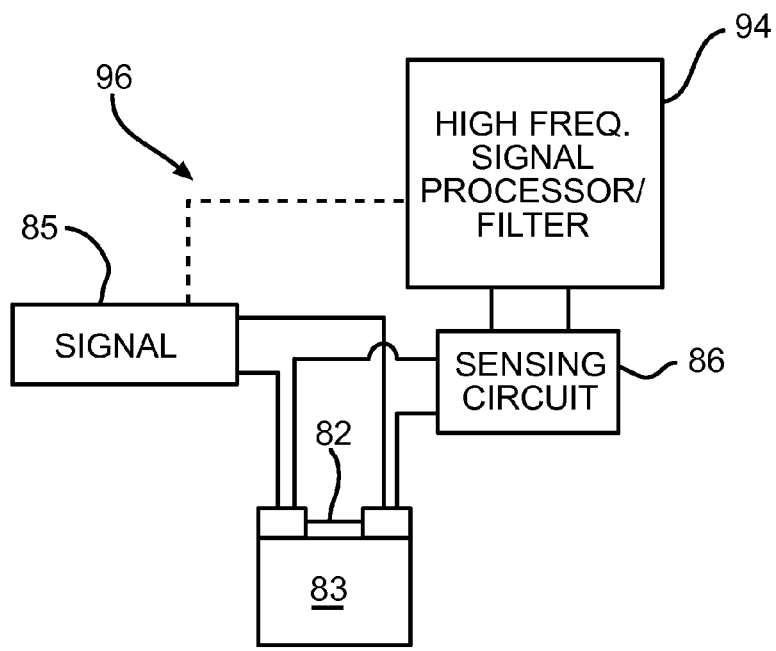
FIG. 22 is a block diagram of high frequency signal processor that functions as filter.

While the acoustic wave excited was described above as operating in a transverse shear mode, other types of acoustic waves may also be excited and used in the MSCAT sensor. Examples of such other types of acoustic waves include longitudinal modes, other shear modes, plate modes and membrane modes. Furthermore, although the particular device described above has a bare sensing surface 56 as shown in FIG. 9, a conductive, or metallic, layer 91, as shown in FIG. 20, such as a metal may be placed upon the sensing surface 56. The conductive layer blocks the electric field produced by the antenna 60 from penetrating the sensing environment and thus allows only mechanical property changes to be measured. Alternately, a layer of sorbent material 92, as shown in FIG. 21, may be placed upon the sensing surface 56. Additionally, while the present invention has been described above in terms of a sensor, it will be appreciated that the present invention also may be utilized in applications relating to a standalone or fundamental component of a high frequency signal processor/filter 94 as shown in the device 96 illustrated in FIG. 22.

EXPERIMENTAL RESULTS

A MSCAT sensor was realized by photolithographically depositing a metallic spiral coil on one side of an AT-quartz wafer, as illustrated in FIG. 12. The metallic spiral coil consisted of 10 turns of a gold film with a chromium adhesion layer. In order to insure that the TSM can be efficiently excited in the MSCAT sensor an RF signal was applied to the monolithic antenna coil with the sensing surface placed in deionized water. The fundamental frequency response, as shown in FIG. 13, and the third harmonic frequency response, as shown in FIG. 14, of the MSCAT sensor were detected by a RITEC Advanced Measurement (RAM) 5000 system. The RAM system was used to both generate and receive acoustic waves in the sensor. The RAM system uses a generator operating mode to generate narrow band RF bursts that are applied to the sensor and then switches to a receiver operating mode to measure the returned signal. When the output is set to the resonant frequency of a device a standing wave is setup within the bulk of the material. This causes a significant change in the received voltage. Since the RAM 5000 system can only operate up to frequencies of 25 MHz, a HP 8571A Network Analyzer was used to monitor the resonant frequency of the MSCAT at higher frequencies.

In order to demonstrate the applicability of the MSCAT sensor the inventor used the sensor to detect changes in the viscosity of liquids. The performance of the MSCAT sensor was then compared to the performance of a standard QCM sensor and an EMPAS sensor with a 16-turn hand wound coil that was fabricated as described in the literature. The MSCAT, QCM and EMPAS sensors were all fabricated from identical one-inch diameter AT-cut quartz wafers obtained from Maxtek, Inc. Fifteen solutions of varying viscosities were made by mixing Karo brand corn syrup with deionized water at varying ratios. The viscosity of each solution was first measured using a Cannon Fenske Routine Viscometer. It was found that the solution viscosities varied over a range of 1 to 27 cP. Each solution was applied to a MSCAT sensor fabricated in accordance with the present invention, a standard QCM sensor and an EMPAS sensor. The change in resonant frequency from the resonant frequency when only de-ionized water was present was measured for each sensor. The QCM sensor response was measured using a Maxtek PLO-10i phase lock oscillator and an EZ FC-705U 100 MHz Universal Counter while the RAM 5000 system was used to drive the MSCAT and EMPAS sensors at the third harmonic.

Figure 15:
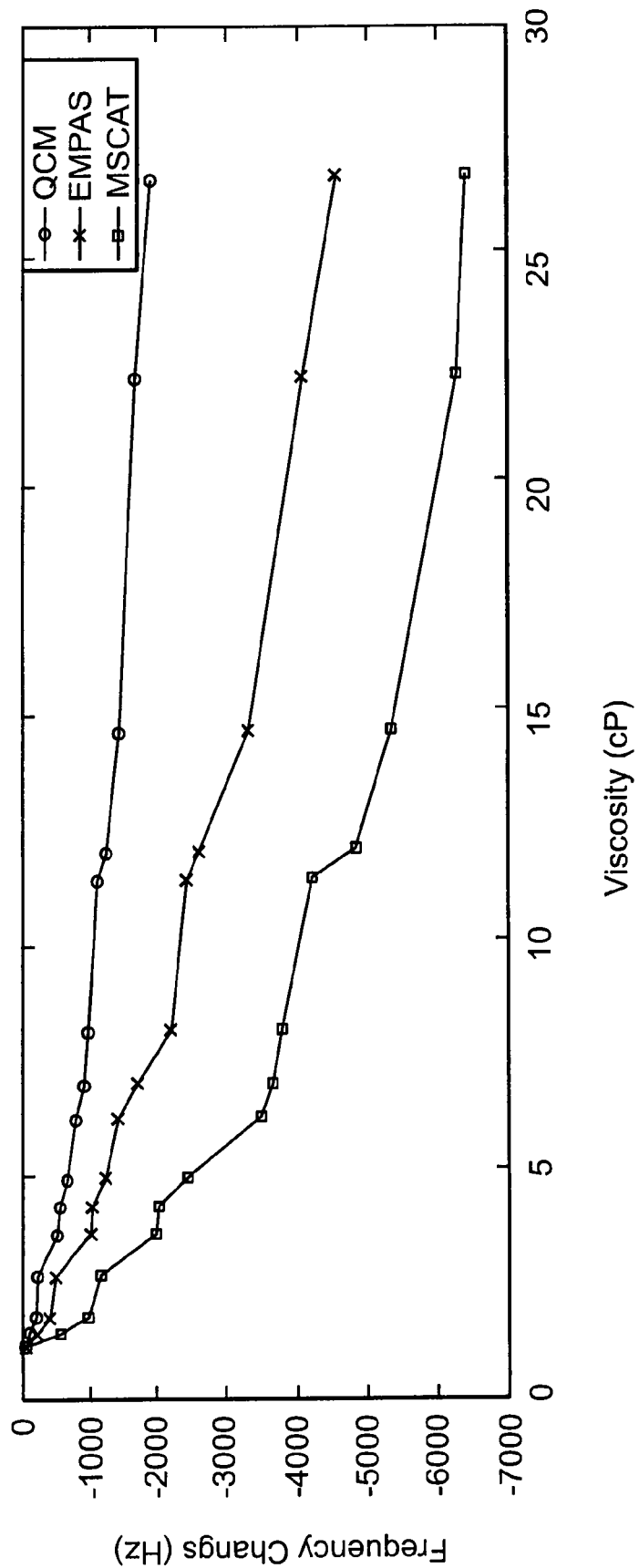
FIG. 15 illustrates the response of an EMPAS, a MSCAST, and a QCM sensor to changes in corn syrup viscosities.

The results of the sensor tests are shown in FIG. 15, where it is seen that the MSCAT sensor had significantly larger responses to viscosity change than either the standard QCM sensor or EMPAS sensor. Specifically, the MSCAT sensor showed an approximately three times larger frequency shift when compared to the standard QCM sensor and an approximately 1.5 times larger frequency shift than the EMPAS sensor. The MSCAT sensor was also very sensitive to small viscosity changes. Since the measurement system is capable of measuring a single Hz shift, the MSCAT sensor should be capable of measuring viscosity changes with an accuracy of about $6\times10^{-4}$ cP.

The reproducibility of the MSCAT sensor results was also determined by exposing the sensor five times to solutions with viscosities between 1 and 7 cP. The measured frequency changes for a given solution were indistinguishable from one another.

Although initial testing focused on the measurement of viscosity, the MSCAT sensor is also capable of detecting electrical changes since there is no metal layer on the sensing surface of the sensor as opposed to the QCM sensor where a metal electrode is placed on top of the AT-Quartz substrate. In the case of the MSCAT sensor the electric field produced by the MSCAT sensor's spiral antenna is capable of penetrating the liquid while the metal electrode on the QCM prevents most of the TSM electric field from penetrating the liquid. This may be the reason why the QCM sensor was the least sensitive to viscosity changes of the sensors tested.

The MSCAT sensor responses to the conductivity of NaCl water solutions in the range of 0 to 0.08 wt % were compared to the responses of a QCM sensor. The MSCAT sensor was operated at its 11th harmonic (55 MHz) and the change in its resonant frequency was monitored by a HP 8571A Network analyzer while the sensor was subjected to the various concentrations of NaCl water solutions. The resonant frequency responses of the QCM sensor to the same liquids were monitored by the Maxtek PLO setup described above. The resonant frequency changes of both sensors with respect to their resonant frequencies in deionized water as a function of NaCl concentration is shown in FIG. 16.

Since the resonant frequency change of the MSCAT sensor is due to both mechanical and electrical property changes in the liquid the NaCl concentrations chosen for this experiment (0 to 0.08% wt) have very small variations in mechanical property changes such as density and viscosity. The frequency shift for a 0.5% wt NaCl solution predicted by perturbation theory was found to be only 5 Hz. It can therefore be assumed that the mechanical properties of the liquid had negligible effects on the frequency response of the two sensors.

Figure 16:
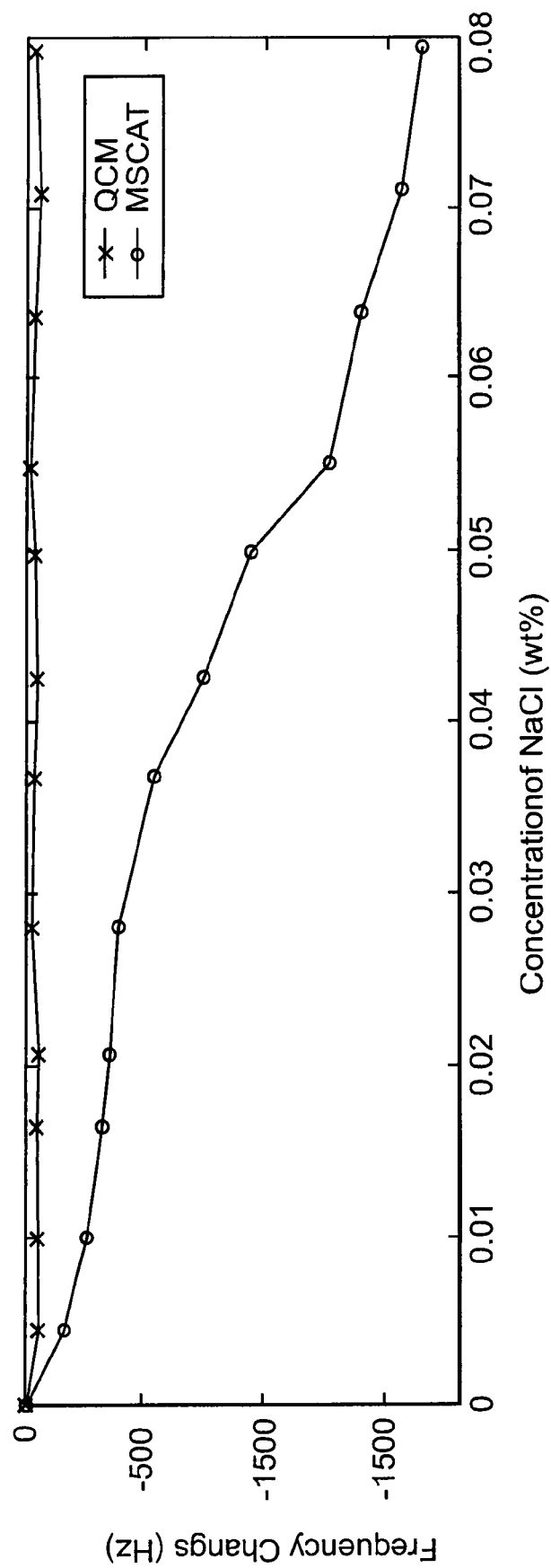
FIG. 16 illustrates sensor response to changes in NaCl concentration for a QCM (fundamental frequency) and a MSCAT ($11^{th}$ Harmonic) sensors.

As can be seen in FIG. 16, the MSCAT sensor was able to measure the changes in the liquid conductivity while the QCM sensor could not. The frequency fluctuations of the QCM sensor for all of the liquids were within the noise level of the sensor. The frequency change of the MSCAT sensor was in excess of 1600 Hz for the 0.08 wt % solution leading the conclusion that the MSCAT sensor is capable of measuring small electrical property changes that a standard QCM sensor cannot measure.

Figure 17:
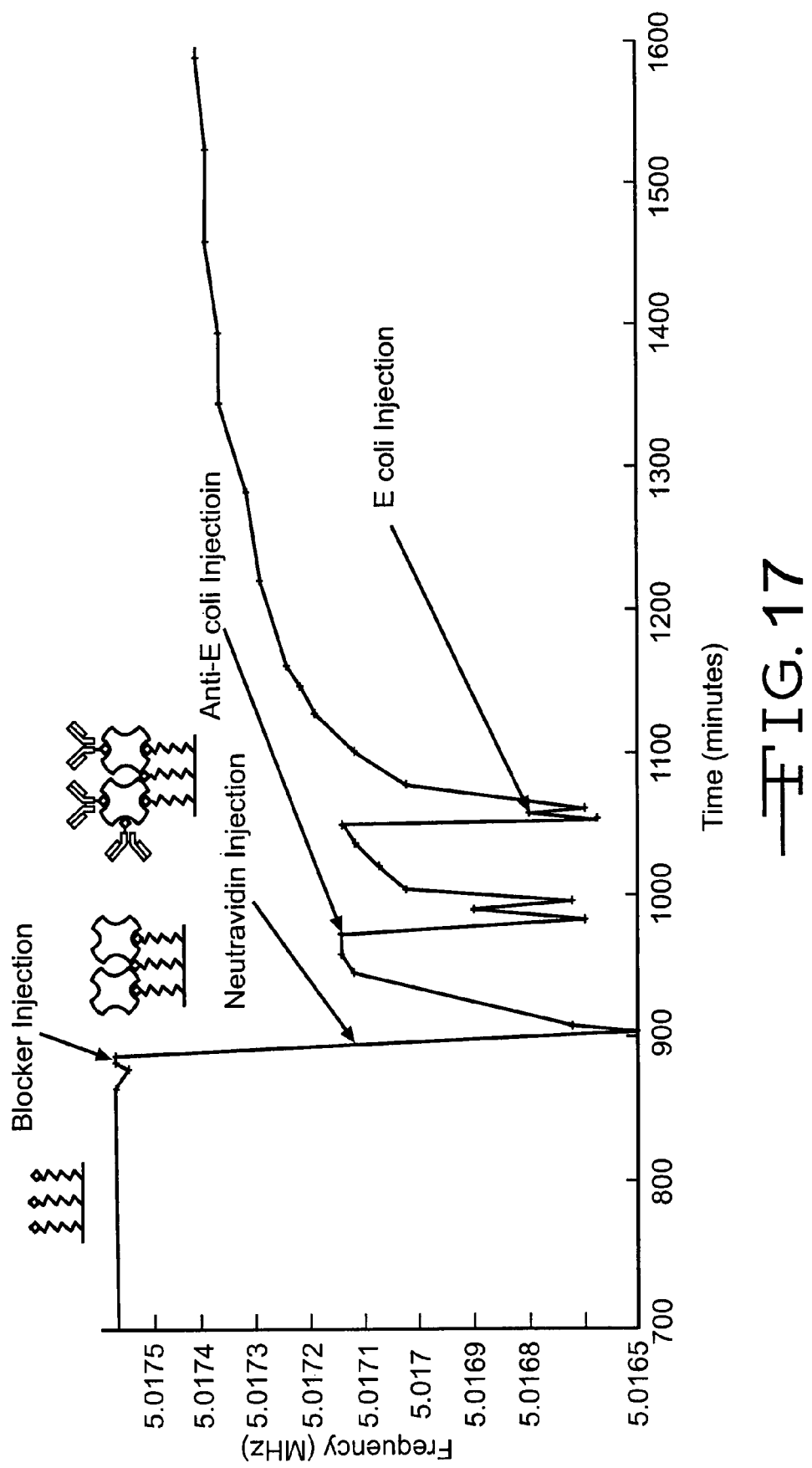
FIG. 17 illustrates the MSCAT frequency response following sequential additions of Biotin, blocker, NeutrAvidin, Anti-*E. coli*, and saturated concentrations of *E. coli*.

As a result of the promising data obtained for the MSCAT sensor the inventor performed preliminary work to determine if the MSCAT sensor can be used for biological sensing; in particular, for detecting *E. coli*. A biochemical film that selectively sorbed *E. coli* was introduced to the MSCAT sensing surface. The fundamental TSM sensor frequency response for operation at the third harmonic is shown in FIG. 14. The MSCAT sensor proved sensitive to changes on its surface from a blocker injection with a PBS+Glycerine rinse, the addition of NeutrAvidin™, an anti-*E. coli* injection with a BSA+PBS rinse, and the introduction of anti-*E. coli* suspension to the MSCAT sensing surface as seen in FIG. 17. Following the introduction of the *E. coli* suspension the frequency increased 715 Hz. To verify that all possible sites were occupied, the sensor's frequency response was monitored during multiple injections of the *E. coli* solution. No noticeable sensor response to further injections of *E. coli* was measured indicating that all binding sites were occupied. Several similar tests performed on a standard QCM sensor resulted in an average frequency shift of about five times less than the shift observed for the MSCAT sensor. The higher sensitivity in the MSCAT sensor is most likely due to the fact that the MSACT sensor can detect both mechanical and electrical property changes occurring due to the *E. coli* attachment. This is in contrast to the standard QCM sensor which can only detect mechanical property changes.

Figure 18:
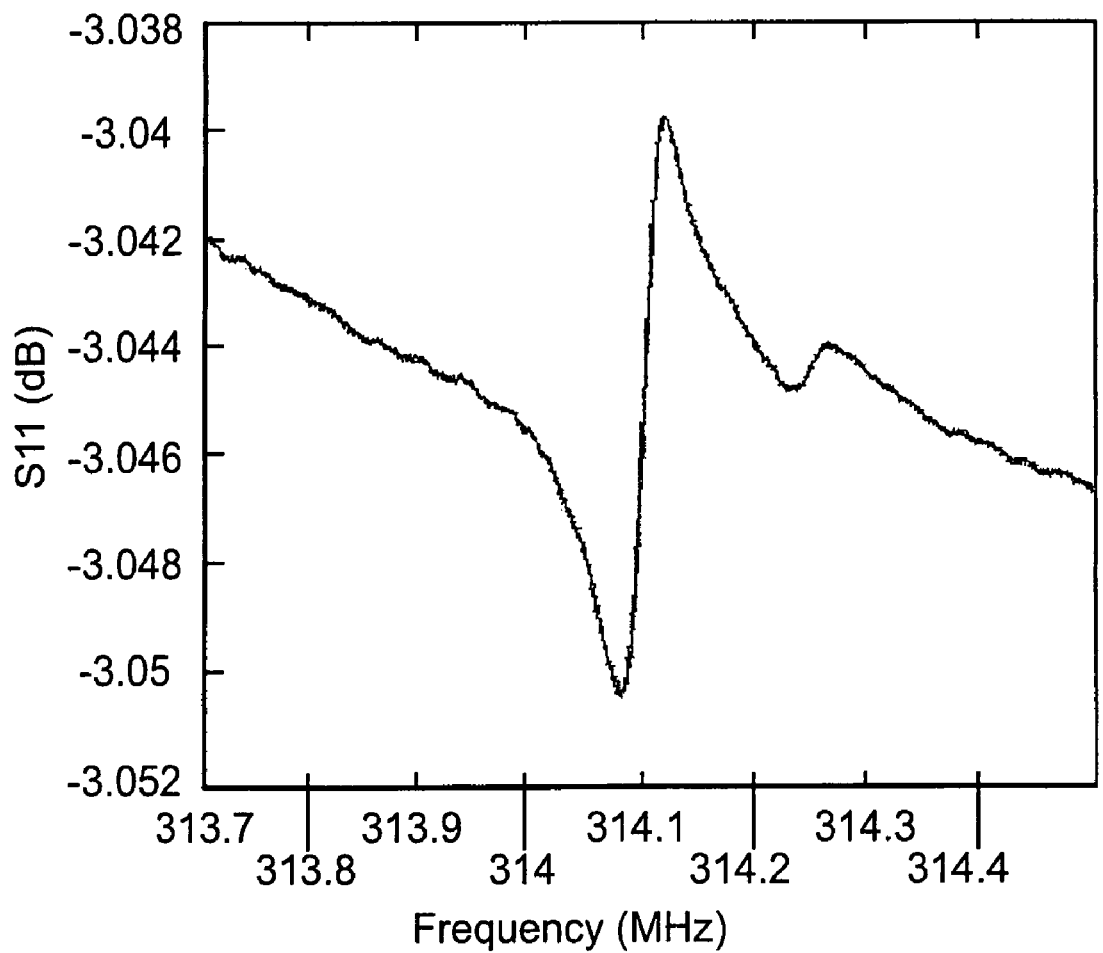
FIG. 18 illustrates the response of a MSCAT sensor operated at the $63^{rd}$ Harmonic.

As described above, the MSCAT sensor data reported above was taken at the 3rd harmonic in the case of the viscosity measurements and *E. coli* detection and at the 11th harmonic in the case of the conductivity measurements. As shown in FIG. 18 it is possible to operate the MSCAT sensor at significantly higher frequencies, in excess of the 63rd harmonic, which was 314 MHz for the quartz crystals used in the test sensors. A HP 8571A was used to measure the voltage reflection coefficient S11 for these measurements. It should be noted that the parallelism and surface finish of the quartz crystals are crucial when the MSCAT sensor is operated at high frequencies. The wavelength of the standing wave that is setup between the faces of the crystal decreases with increasing frequency. If the crystal faces are not parallel or if the surfaces are not flat destructive interference will not allow a standing wave to form at higher harmonics. In fact the inventor was not able to excite the MSCAT sensor higher than the 9th harmonic using standard quartz blanks that were manufactured by Sawyer Technical Materials, LLC (Eastlake Ohio) for QCM applications. It was only after the inventor fabricated the MSCAT sensor on crystals from Lap-Tech (Bowmanville, Ontario) that had an optical polish and faces that were parallel to within 4 light bands that we were able to excite higher harmonics.

The experimental results obtained by the inventor are significant because it is the first demonstration of a monolithic spiral coil being used to excite bulk acoustic waves in a piezoelectric substrate. The present results also clearly demonstrate that the MSCAT sensor is superior to other Bulk Acoustic Wave (BAW) sensors in measuring viscosity in liquids. Application of the MSCAT sensor to detect chemical analytes critical to areas such as homeland security, environmental safety, agriculture, and medicine will determine the ultimate potential of the MSCAT sensor.

The present invention has many advantages as a monolithic device. First, the exciting antenna configuration is not exposed to the adjacent environment. Secondly, and most importantly, it is possible to operate a device in accordance with the present invention at very high frequencies that may exceed 1 GHz by exciting higher harmonics with the application of a high frequency RF signal to the exciting antenna. In addition, the present invention does not require single or multiple layers or excitation schemes external to the piezoelectric substrate, making it a much simpler device to manufacture.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. An acoustic wave device comprising:
   a substrate formed from a piezoelectric material;
   a single strip of electrically conductive material having a generally spiral shape formed upon a surface of said substrate, said electrode operative to propagate acoustic waves; and
   a pair of electrical connectors, each of said electrical connectors being attached opposite ends of said strip of electrically conductive material.

2. The device according to claim 1 wherein said strip of electrically conductive material is formed as one of the group of a spiral coil, an oval shaped coil, an elliptically shaped coil, a triangle shaped claim, a polygonal shaped coil and a quadrilateral shaped coil.

3. The device according to claim 2 wherein said substrate is a disc formed from one of the group of AT-quartz, lithium tantalite, lithium niobate, potassium niobate, gallium phosphate and one of the members of the langasite family of crystals.

4. The device according to claim 3 wherein said strip of electrically conductive material is photolithographically deposited upon said surface of said substrate.

5. The device according to claim 4 wherein said strip of electrically conductive material is formed from one of the group of gold, chromium, platinum, silver, copper, zirconium, aluminum, zinc, lead, and palladium.

6. The device according to claim 1 wherein said substrate has a sensing surface that is exposed to an environment to be sensed and an excitation surface that is opposite from said sensing surface and further wherein said strip of electrically conductive material is formed upon said excitation surface of said substrate.

7. The device according to claim 6 further including a layer of a sorbent material deposited upon said sensing surface, said sorbent material being selected to absorb a measurand contained within the environment being sensed, said absorbed measurand changing an operative characteristic of the sensor such that the change in said operative characteristic can be correlated with said measurand.

8. The device according to claim 6 further including a metallic layer deposited upon said sensing surface.

9. The device according to claim 6 further including an adhesive layer disposed between said substrate and said strip of electrically conductive material.

10. The device according to claim 9 wherein said adhesive layer includes chromium.

11. The device according to claim 9 wherein the device is a stand-alone component of a high frequency signal filter.

12. The device according to claim 9 wherein the device is a fundamental component of a high frequency signal processor that functions as a filter.

13. The device according to claim 9 wherein said sensing and excitation surfaces are parallel.

14. The device according to claim 13 wherein said sensing and excitation surfaces are parallel to a tolerance within four light bands.

15. The device according to claim 13 wherein said sensing and excitation surfaces are flat.

16. The device according to claim 15 wherein said sensing and excitation surfaces are polished.

17. A testing apparatus comprising:
   an acoustic wave device having a single strip of electrically conductive material formed upon a surface of a substrate formed from a piezoelectric material, said strip of electrically conductive material operative to propagate acoustic waves;
   a pair of electrical connectors, each of said electrical connectors being attached opposite ends of said strip of electrically conductive material;
   a variable frequency oscillator connected to said strip of electrically conductive material by said pair of electrical connectors;
   a sensing circuit connected to said oscillator; and
   a controller connected to said oscillator and said sensing circuit, said controller operative to sweep said oscillator through a range of frequencies that include a characteristic frequency of said acoustic device while monitoring a parameter of said acoustic device.

18. The testing apparatus according to claim 17 wherein said characteristic frequency of said acoustic device is a resonant frequency of said acoustic device.

19. The testing apparatus according to claim 18 wherein said monitored parameter of said acoustic device includes a shift of said resonant frequency.

20. The testing apparatus according to claim 19 wherein said characteristic frequency of said acoustic device is a harmonic of a resonant frequency of said acoustic device.

21. The testing apparatus according to claim 20 wherein said monitored parameter of said acoustic device includes a shift of said harmonic of said resonant frequency.

22. A method for fabricating an acoustic wave device comprising the steps of:
   (a) providing a piezoelectric crystal:
   (b) cutting the crystal to form a substrate having a reference surface for generation of acoustic waves and a sensing surface for immersion into an environment that contains a measurand of interest, the sensing surface being parallel to the reference surface; and
   (c) depositing a single strip of electrically conductive material upon the reference surface of the substrate with the single strip of conductive material being the only conductive material deposited upon a surface of the substrate.

23. The method according to claim 22 further including, subsequent to step (c), the step of:

(d) attaching at least one electrical lead to the strip of electrically conductive material.

24. A method for fabricating an acoustic wave device comprising the steps of:
(a) providing a piezoelectric crystal:
(b) cutting the crystal to form a substrate having a reference surface for generation of acoustic waves and a sensing surface for immersion into an environment that contains a measurand of interest, the sensing surface being parallel to the reference surface;
(c) applying an adhesion layer to the reference surface of the substrate and
(d) depositing a single strip of electrically conductive material upon the reference surface of the substrate.

25. The method according to claim 24 wherein step (b) also includes, subsequent to cutting the crystal, polishing the reference and sensing surfaces.

* * * * *